United States Patent
Baham

(10) Patent No.: US 10,117,772 B2
(45) Date of Patent: Nov. 6, 2018

(54) FEMALE URINATION AID

(71) Applicant: John Baham, Eunice, LA (US)

(72) Inventor: John Baham, Eunice, LA (US)

( * ) Notice: Subject to any disclaimer, the term of this patent is extended or adjusted under 35 U.S.C. 154(b) by 0 days.

(21) Appl. No.: 15/282,325

(22) Filed: Sep. 30, 2016

(65) Prior Publication Data

US 2017/0014261 A1     Jan. 19, 2017

Related U.S. Application Data

(62) Division of application No. 13/031,696, filed on Feb. 22, 2011, now Pat. No. 9,480,595.

(51) Int. Cl.
*A61F 5/455* (2006.01)
*A47K 10/18* (2006.01)

(52) U.S. Cl.
CPC ............ *A61F 5/4556* (2013.01); *A47K 10/18* (2013.01)

(58) Field of Classification Search
CPC .................................................... A61F 5/4556
USPC .............................................. 4/144.1–144.4
See application file for complete search history.

(56) References Cited

U.S. PATENT DOCUMENTS

| | | | | |
|---|---|---|---|---|
| 4,531,245 A * | 7/1985 | Lowd | ..................... | A47K 11/00 141/337 |
| 6,572,827 B2 * | 6/2003 | Wilkinson | .............. | B01L 3/502 141/1 |
| 6,904,621 B2 * | 6/2005 | Otto | ........................ | A61F 5/451 4/144.1 |
| 7,251,843 B2 * | 8/2007 | Malloy | .................. | A47K 11/12 4/144.1 |
| 2005/0097660 A1 * | 5/2005 | Malloy, Sr. | ............ | A61G 9/006 4/144.1 |

* cited by examiner

*Primary Examiner* — Christine Skubinna
(74) *Attorney, Agent, or Firm* — Law Office of Jesse D. Lambert, LLC

(57) ABSTRACT

A female urination aid to enable a female to urinate from a standing position. The invention, in one embodiment, has a disposable funnel, typically made of paper or similar material, which fits into a reusable holder, which enables the funnel to be held against the body. The funnel may include an attached pad of wiping paper. In a second, reusable or multi-use embodiment, the funnel portion of the apparatus is of a reusable material such as plastic. A fluid container for holding a cleaning solution conveniently snaps onto the funnel, forming an easy to carry kit. Wiping paper may be attached to the funnel, so as to form a readily usable kit.

4 Claims, 3 Drawing Sheets

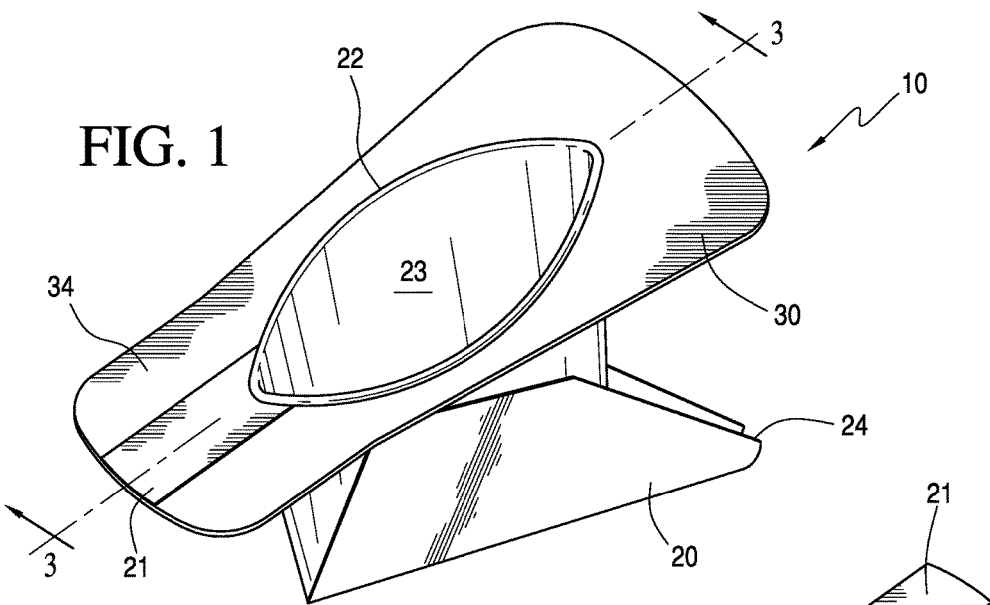
FIG. 1
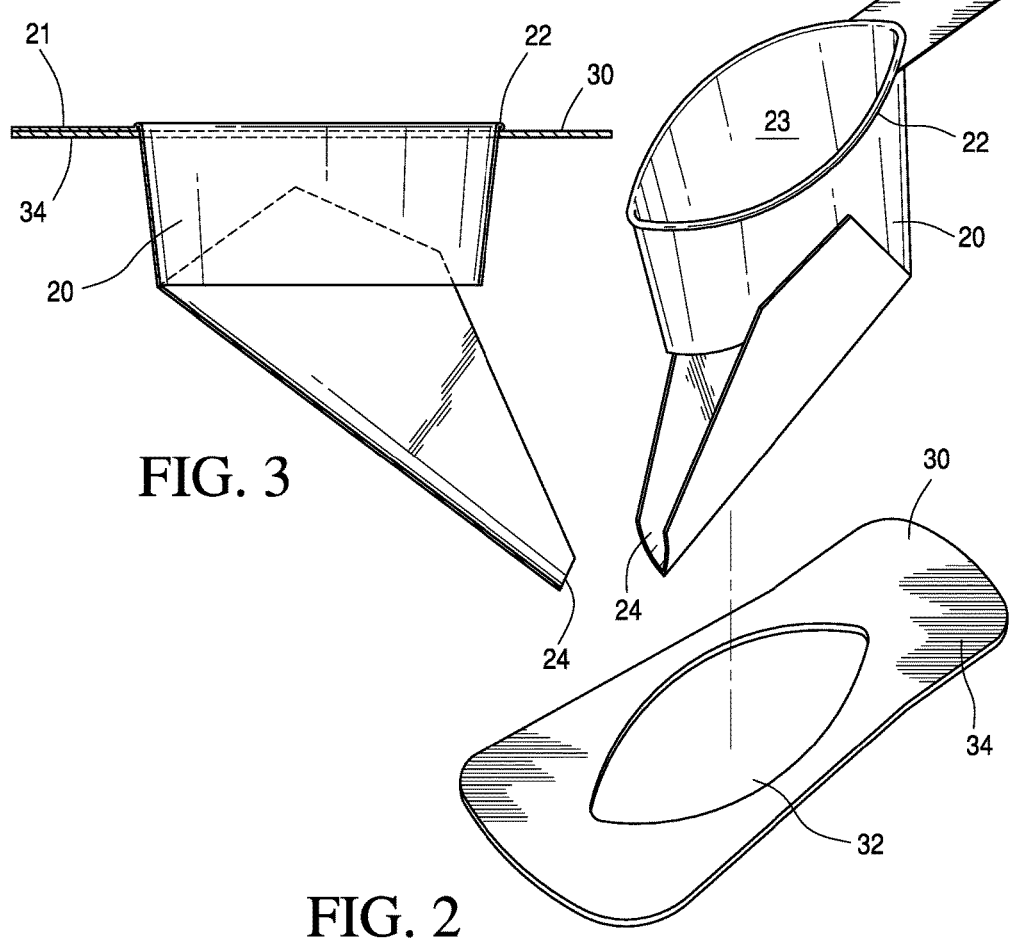
FIG. 3
FIG. 2

FEMALE URINATION AID

CROSS REFERENCE TO RELATED APPLICATIONS

This patent application is a divisional application of co-pending patent application Ser. No. 13/031,696.

BACKGROUND

Field of the Invention

This invention relates, generally, to apparatus for aiding human females in the urination process. More specifically, this invention relates to an apparatus to enable females to urinate from a standing position, thereby avoiding contact with a toilet seat.

Related Art

As is well known, restrooms, particularly public restrooms, are frequently not well maintained and can become unclean. Even restrooms which are regularly cleaned can become unclean during periods of heavy use, such as at sporting events, concerts, etc.

As a result, restroom patrons, namely females, are often reluctant to sit upon toilet seats when urinating. Various means have been developed in order to address this issue. One such means is disposable toilet seat covers. However, these are cumbersome to use, must be kept in stock, etc.

Another way that this problem has been addressed has been via an apparatus that permits the female to urinate without sitting on the toilet, i.e. from a standing position. Generally, in order to enable this action, a means must be provided to contain the urine stream and channel it into the toilet. Most prior art efforts to address this problem comprise, in one form or another, a funnel apparatus which the user holds against her body, and directs the opening thereof to the toilet.

The present invention addresses various limitations and drawbacks in the known prior art apparatus.

BRIEF DESCRIPTION OF THE DRAWINGS

FIG. 1 is a perspective view of one embodiment (disposable funnel) of the apparatus.

FIG. 2 is another perspective view, showing the disposable funnel removed from its position within the reusable holder.

FIG. 3 is a side view of the funnel in place within the holder.

DESCRIPTION OF THE PRESENTLY PREFERRED EMBODIMENT(S)

Figure 4:
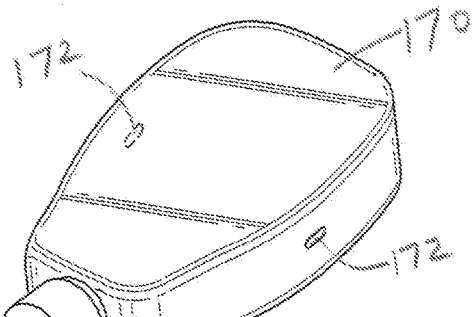
FIG. 4 is a perspective view of a second embodiment of the invention.

The present invention comprises two broad embodiments: the first embodiment to be described is one comprising a disposable funnel element, held within a reusable holder; the second embodiment is a reusable apparatus, which may be cleaned between uses.

Disposable Embodiment

FIGS. 1-3 show the disposable embodiment. Urination aid 10 comprises a funnel 20, which fits into and is held by a holder 30 in use. Funnel 20 is preferably formed from a relatively thin, collapsible and disposable material. Suitable materials include paper (which may be coated with wax or similar substance to make it substantially impervious to liquid), plastics, or other similar collapsible, low cost materials. As can be understood from the drawings, funnel 20 may be collapsed into a flat position for carrying, then opened up or expanded for use. Funnel 20 has an opening 23, and tapers to an outlet 24. Preferably, funnel 20 has a protruding rim 22 about its upper mouth portion, encircling opening 23.

Holder 30 is formed of a relatively thin but rigid sheet material, stiff enough to hold funnel 20 in place, as later described. Holder 30 generally comprises an elongated, generally rectangular plate element, which may be shaped to better fit against a female anatomy, with rounded corners, etc., such that a urine stream can be directed into opening 23 of funnel 20 when funnel 20 is held against the female anatomy. Holder 30 comprises an opening 32 into which funnel 20 is inserted. Opening 32 is sized and shaped to closely accommodate funnel 20, when funnel 20 is opened and inserted through opening 32. Opening 32 may be substantially circular, or preferably somewhat elongated as in the drawings, to better accommodate funnel 20 (opening 23 typically being elongated when opened). Holder 30 can be made of various materials, including thin (but rigid) plastic sheet material, thin metal sheet, etc. Preferably, holder 30 is of a material which can sustain being wet for cleaning, etc. If desired, holder 30 can be pre-formed into a slightly curved shape, to better fit against the female anatomy.

To use this embodiment of the apparatus, funnel 20 is expanded (assuming that it was initially in a flattened shape), and fitted into opening 32 until rim 22 contacts plate 30, which prevents funnel from going through plate 30. While in a standing position, positioned as appropriate over a toilet or urinal, the user then places plate 30 against her body, namely covering the pubic region, with opening 23 in funnel 20 positioned so as to receive the urine stream. The user can then urinate, and the urine stream is directed via funnel 20, out of outlet 24 into the toilet or urinal. After use, funnel 20 can be removed from plate 30 and discarded.

It is to be understood that since funnel 20 is collapsible, a number of them can be carried in a dispenser, in turn carried in a purse, handbag, etc. by the user. Alternatively, funnel 20 may be held in a dispenser within a bathroom, for use by the patrons thereof. Funnel 20 may be made of coated paper, folded so that funnel 20 may be flattened for compact storage.

If desired, funnel 20 may comprise a combined extended lip and wiping paper 21 fixed thereto (denoted by the cross hatched portion shown in FIGS. 1 and 3). If so, lip and wiping paper 21 would be supported by front lip 34 of plate 30, so that the user could exert sufficient force via plate 30 to wipe private areas as desired. Then, funnel 20 with lip and wiping paper 21 thereon can be discarded.

Reusable, Multi-Use Embodiment

Figure 5:
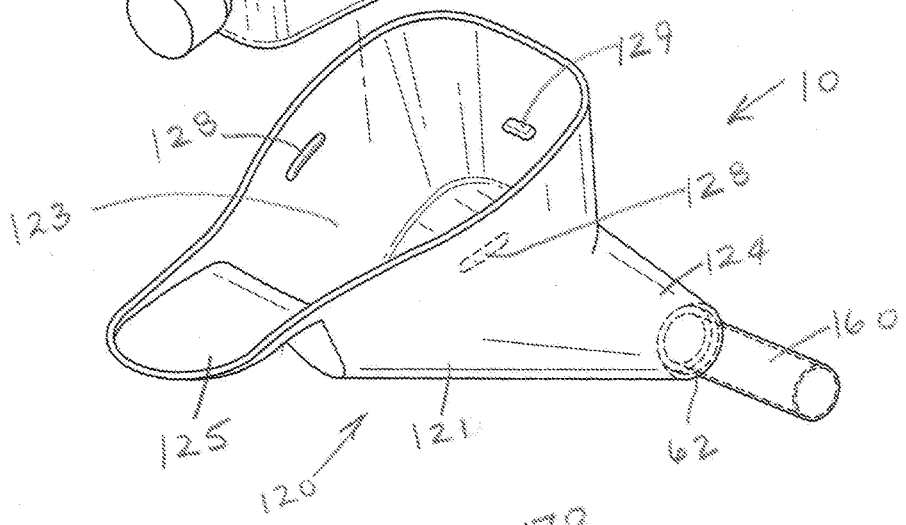
FIG. 5 is a side view of the second embodiment of FIG. 4.
Figure 5:
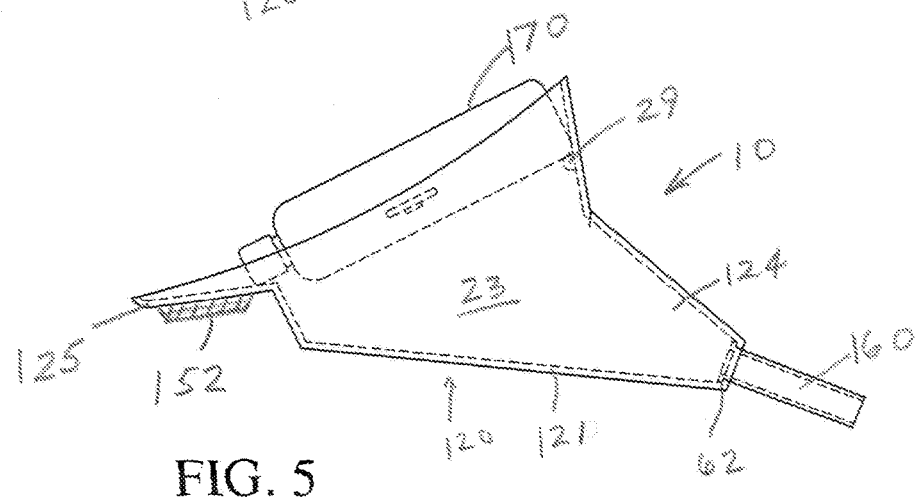
Figure 6:
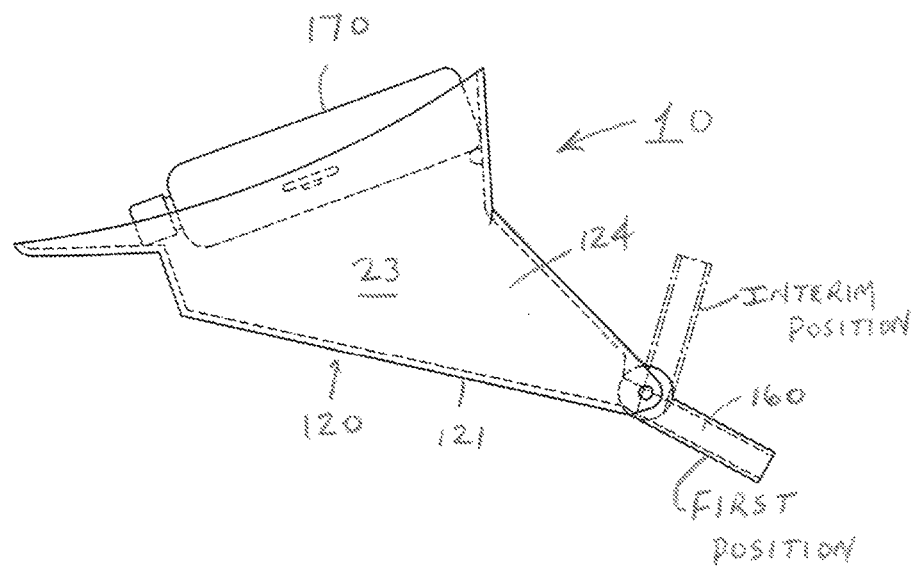
FIG. 6 shows an alternate embodiment of the invention.

Yet another embodiment is shown in FIGS. 4 and 5. Here, funnel 120 is preferably formed of a lightweight, waterproof material, such as thin but rigid plastic, by molding or other means known in the art. Funnel 120 comprises a main body 121, comprising a central opening 123 which tapers down to an outlet portion 124. In order to provide sufficient length of the apparatus to place the urine stream where desired, extension tube 160 is preferably provided. In the preferred embodiment, extension tube 160 is slidably disposed in outlet portion 124, and is held in place by a shoulder 62 which bottoms out within neck portion 124. It is understood that extension tube 160 is movable between a first position in which extension tube 160 extends from outlet portion 124 (as in FIGS. 4 and 5), and a second position in which extension tube 160 can be retracted to a position within main body 121, to make the apparatus more compact when not in use. FIG. 6 shows an alternative embodiment of extension tube 160, wherein extension tube 160 can be rotated between a first position (noted), generally directing a urine stream out of neck portion 124; and a second position, rotated substantially back against neck portion 124 (an interim position is shown in phantom lines and noted on the drawing).

Funnel 120 also preferably has a lower lip portion 125, typically relatively narrow in width, to ease fitting funnel 120 at least partially between the user's upper legs and against the body. If desired, wiping paper 152 can be carried in a holder positioned on the underside of lip portion 125 (or at some other convenient location on funnel 120). This makes it convenient for the user to clean herself after use, without depending upon a supply of wiping paper being present in the bathroom.

It is understood that this embodiment of the invention is reusable, and it would generally be desired to clean it between uses. To facilitate that process, fluid container 170 is provided, which is attachable to funnel 120. In the preferred embodiment shown, fluid container 170 can be conveniently held together with funnel 120 by being shaped to generally fit snugly within central opening 123. As can be seen in FIGS. 4 and 5, fluid container 170 may be provided with small projections 172, which snap into corresponding recesses 128 within central opening 123, and further fluid container 170 abuts shoulder 129 within central opening 123. The combination of the projections fitting into the recesses, and abutting shoulder 129, keep fluid container 170 firmly in position. It is understood that other embodiments are possible, where fluid container 170 essentially snaps over central opening 123, and may comprise a lip over the outside rim of central opening 123. A cleaning solution may be carried in fluid container 170, which may be squirted into funnel 120 after use (fluid container 170 of course being removed while the apparatus is in use), funnel 120 then being rinsed for cleaning. It can be appreciated that fluid container 170 being snapped together with funnel 120 makes a convenient "kit" for the user, which may be carried in a purse, handbag, or belt-mounted holder.

CONCLUSION

While the preceding description contains many specificities, it is to be understood that same are presented only to describe some of the presently preferred embodiments of the invention, and not by way of limitation. Changes can be made to various aspects of the invention, without departing from the scope thereof. For example, dimensions and shapes of the various components of the invention may be varied to suit particular uses; and materials may be varied as desired.

Therefore, the scope of the invention is to be determined not by the illustrative examples set forth above, but by the appended claims and their legal equivalents.

I claim:

1. A multi-use female urination aid, comprising:
    a funnel shaped main body comprising a central opening, and a rim surrounding said central opening, said rim sized and shaped to fit against the human female anatomy so that a urine stream may be directed into said central opening, said main body further comprising an extended outlet portion, said main body further comprising an extended lip portion sized and shaped to fit at least partially between a user's legs, thereby assisting in holding said main body in place during use; and
    a fluid container removably attached to said funnel, wherein said fluid container is sized and shaped to substantially cover said central opening of said main body and be removably held thereagainst, said fluid container adapted to contain a quantity of cleaning solution therein, whereby said fluid container is completely removed and detached from said main body before use of said multi-use female urination aid, and after use of said multi-use female urination aid a quantity of said cleaning solution is used to rinse said multi-use female urination aid, after which said fluid container is again attached to said funnel so as to substantially cover said central opening of said main body.

2. The female urination aid of claim 1, wherein said main body further comprises a single section telescoping extension tube, which in a first position is extended from said outlet portion until a shoulder on said extension tube rests against a portion of said outlet portion, and in a second position is retracted within said main body so as not to extend therefrom.

3. The female urination aid of claim 2, wherein said main body comprises an extended lip and a quantity of wiping paper held thereon, whereby said wiping paper may be used to clean the female anatomy.

4. The female urination aid of claim 1, wherein said main body further comprises a rotating extension tube, which can be rotated between a first position extending from said outlet portion, and a second position rotated substantially back against said outlet portion.

* * * * *